United States Patent
Beard et al.

(10) Patent No.: US 7,126,333 B2
(45) Date of Patent: Oct. 24, 2006

(54) METHOD AND APPARATUS FOR CORRECTING RINGING IN NMR SIGNALS

(75) Inventors: David R. Beard, Houston, TX (US); Daniel T. Georgi, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 52 days.

(21) Appl. No.: 10/827,183

(22) Filed: Apr. 19, 2004

(65) Prior Publication Data

US 2005/0231198 A1   Oct. 20, 2005

(51) Int. Cl.
   G01V 3/00    (2006.01)
(52) U.S. Cl. ..................................... 324/303
(58) Field of Classification Search ................. 324/303
   See application file for complete search history.

(56) References Cited

U.S. PATENT DOCUMENTS

| | | | |
|---|---|---|---|
| 5,023,551 A | 6/1991 | Kleinberg et al. | 324/303 |
| 5,365,171 A | 11/1994 | Buess et al. | 324/307 |
| 5,596,274 A | 1/1997 | Sezginer | 324/303 |
| 5,712,566 A | 1/1998 | Taicher et al. | 324/303 |
| 6,121,774 A | 9/2000 | Sun et al. | 324/303 |
| 6,204,663 B1 | 3/2001 | Prammer | 324/303 |
| 6,377,042 B1 | 4/2002 | Menger et al. | 324/303 |
| 6,452,389 B1 * | 9/2002 | Edwards | 324/303 |
| 6,466,013 B1 | 10/2002 | Hawkes et al. | 324/303 |
| 6,525,534 B1 * | 2/2003 | Akkurt et al. | 324/303 |
| 6,541,969 B1 | 4/2003 | Sigal et al. | 324/303 |
| 6,570,381 B1 | 5/2003 | Speier et al. | 324/303 |
| 6,646,438 B1 | 11/2003 | Kruspe et al. | 324/303 |
| 6,690,167 B1 * | 2/2004 | Reiderman et al. | 324/314 |
| 6,897,651 B1 * | 5/2005 | Reiderman et al. | 324/303 |
| 6,903,547 B1 * | 6/2005 | Sigal et al. | 324/303 |
| 2002/0196017 A1 | 12/2002 | Akkurt et al. | 324/303 |
| 2003/0038631 A1 | 2/2003 | Kruspe et al. | 324/303 |
| 2003/0210043 A1 | 11/2003 | Freedman | 324/303 |
| 2004/0008027 A1 * | 1/2004 | Prammer | 324/303 |
| 2005/0068027 A1 * | 3/2005 | Beard | 324/303 |

\* cited by examiner

*Primary Examiner*—Diego Gutierrez
*Assistant Examiner*—Dixomara Vargas
(74) *Attorney, Agent, or Firm*—Madan, Mossman & Sriram, P.C.

(57) ABSTRACT

Estimates of ringing produced by short recovery pulse sequences (CPMG or modified CPMG) are used to improve the effects of ringing in a conventional CPMG or modified CPMG sequences. This is an effective method for removal of ringing when the ringing is varying over a time interval that would be spanned by a phase alternated pair of conventional sequences. By use of frequency dithering, ringing due to the excitation pulse and the refocusing pulses can be removed.

34 Claims, 5 Drawing Sheets

---

Measure the ringing for each frequency in the dithered data set. ⟶ 501

Rotate each ringing measure through
$$\phi(\delta f) = -\pi \cdot \delta f \cdot TE$$
⟶ 503

Average the rotated ringing measures and record (as a vector) ⟶ 505

METHOD AND APPARATUS FOR CORRECTING RINGING IN NMR SIGNALS

BACKGROUND OF THE INVENTION

1. Field of the Invention

The invention is related to the field of nuclear magnetic resonance exploration of oil wellbore. In particular, the invention is a method of correcting for ringing effects inherent in magnetic pulse sequence testing.

2. Description of the Related Art

A variety of techniques are utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One recently evolving technique involves utilizing Nuclear Magnetic Resonance (NMR) logging tools and methods for determining, among other things, porosity, hydrocarbon saturation and permeability of the rock formations. The NMR logging tools are utilized to excite the nuclei of the liquids in the geological formations surrounding the wellbore so that certain parameters such as spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

The NMR tools generate a uniform or near uniform static magnetic field in a region of interest surrounding the wellbore. NMR is based on the fact that the nuclei of many elements have angular momentum (spin) and a magnetic moment. The nuclei have a characteristic Larmor resonant frequency related to the magnitude of the magnetic field in their locality. Over time the nuclear spins align themselves along an externally applied magnetic field. This equilibrium situation can be disturbed by a pulse of an oscillating magnetic field, which tips the spins with resonant frequency within the bandwidth of the oscillating magnetic field away from the static field direction. The angle θ through which the spins exactly on resonance are tipped is given by the equation:

$$\theta = \gamma B_1 t_p. \quad (1)$$

where $\gamma$ is the gyromagnetic ratio, $B_1$ is the effective field strength of the oscillating field and $t_p$ is the duration of the RF pulse.

After tipping, the spins precess around the static field at a particular frequency known as the Larmor frequency $\omega_0$, given by $$\omega = \gamma B_0 \quad (2)$$

where $B_0$ is the static field intensity. At the same time, the spins return to the equilibrium direction (i.e., aligned with the static field) according to an exponential decay time known as the spin-lattice relaxation time, or longitudinal relaxation time, $T_1$. For hydrogen nuclei, $\gamma/2\pi=4258$ Hz/Gauss, so that a static field of 235 Gauss would produce a precession frequency of 1 MHz. $T_1$ of fluid in pores is controlled totally by the molecular environment and is typically ten to one thousand milliseconds in rocks.

Typically, measurement of NMR related phenomena in the earth formation is performed by allowing some time for the static magnetic field to polarize nuclei in the formation in a direction substantially along the direction of the static magnetic field. A first one of the RF pulses passed through the antenna has a magnitude and duration selected to reorient the nuclear magnetization by about 90 degrees from its previous orientation. This pulse is referred to in the prior art as the A-pulse, the 90°-pulse, and the excitation pulse, among others. After a selected time, successive RF pulses are passed through the antenna, each of these having a magnitude and duration selected to reorient the nuclear spin axes by about 180 degrees from their immediately previous orientations in order to enable the nuclear spin axes to "rephase" or realign with each other. These pulse rephrasing pulses are referred to in the prior art as the B-pulses, the 180°-pulses, and refocusing pulses, among others. The induced signals, known as "spin echoes", are generally measured during the time interval between each successive one of the "180 degree" RF pulses. The succession of spin echo measurements is generally known as a "sequence". The amplitude of the spin echo signals, and the rate at which the spin echo amplitudes change during a measurement sequence, are related to properties of interest of the earth formations, such as fractional volume of pore space (porosity) and the properties of fluids present in the pore spaces. The frequency of the RF magnetic field needed to reorient the nuclear magnetization, which is the frequency of the spin echo signals, is related to the amplitude of the static magnetic field and a factor, known as the gyromagnetic ratio $\gamma$, which is unique to each isotope. For evaluation of earth formations, the static magnetic field amplitude and RF magnetic field frequency are typically selected to excite NMR phenomena in hydrogen nuclei, although other nuclei may be used for NMR evaluation of earth formations.

Exciting the antenna with RF power pulses in the presence of a strong static magnetic field causes mechanical excitation of the antenna. Mechanical excitation of the antenna leads to excitation of a signal, called "ringing", in the antenna. The ringing is unrelated to NMR phenomena, and frequently has a very large amplitude. The amplitude of the ringing is often highest right after application of each RF pulse, and is of such a magnitude as to make it difficult to measure the amplitude of NMR induced signals. Reducing the effects of ringing on NMR measurement is very important in well logging applications, among others, because significant information about the properties of the earth formations are determined by the amplitudes of spin echoes occurring shortly after the RF pulses.

Apparatuses which reduce ringing effects by way of tool design are discussed, for example in U.K. Patent Publication GB2310724A, of Taicher, and U.S. Patent Publication 20030038631 of Kruspe. Methods for removing the effects of acoustic ringing in Nuclear Quadrupole Resonance techniques are discussed in U.S. Pat. No. 5,365,171, of Beuss.

Several methods are known in the art for removing ringing effects. One class of such methods includes creating a phase difference between the ringing signal and the NMR induced signals, and summing or "stacking" multiple sets of measurements to reduce the amplitude of the ringing signal in the output. One commonly used measurement sequence used in evaluation of earth formations is known as "phase alternate pairs" (PAPS). PAPS sequences include performing a measurement sequence as just described including a 90 degree RF pulse followed by successive 180 degree pulses. After a selected wait time, another such measurement sequence is performed, but with the polarity of the 90 degree pulse reversed. Stacking the two sets of measurements substantially cancels the ringing signal. Such a method is described, for example, in U.S. Pat. No. 5,596,274 to Sezginer and U.S. Pat. No. 5,023,551 to Kleinberg et al.

In traditional PAPS techniques, first an acquisition is performed at time t and the resulting measurement, m(t) contain both useful echo data, e(t), and corrupting ringing data, r(t), resulting in $$m(t)=e(t)+r(t). \tag{4}$$

After this acquisition, it is typically necessary to wait a time for the measured material to recover, leading to a long repetition rate, $tr_l$. The acquisition is repeated, this time with identical parameters, except that the phase of the excitation pulse is moved through 180°. This has the effect of changing the sign of the echo data, but it does not affect the ringing which is primarily created by the refocusing pulses. So:

$$m(t+tr_l)=-e(t+tr_l)+r(t+tr_l). \tag{5}$$

The PAP technique is to subtract these two measurements, i.e.

$$PAPS\left(t+\frac{tr_l}{2}\right) = \frac{m(t)-m(t+tr_l)}{2} = \frac{e(t)+e(t+tr_l)}{2} + \frac{r(t)-r(t+tr_l)}{2} \tag{6}$$

If the ringing is constant or very slowly changing, the PAPS result is the average of the two echo signals and contains little or no ringing signal. Usually, the material that is ringing is within the instrument (sensor or electronics) and the assumption that the ringing changes slowly with time. However, in some circumstances, e.g. metal debris in the well, the ringing material may be external to the instrument. This external material typically moves with respect to the instrument and therefore changes the ringing during time interval between the pulse sequences. The duration of time between the first and second sequences of the PAPS sequence must necessarily be large to allow for adequate spin-lattice relaxation before the second sequence. The extended length of time also leads to different material being tested in each sequence of the PAPS because of the motion of the measurement device through the borehole. The wait time, $tr_l$, thereby limits the effectiveness of the results. Another disadvantage of the PAPS sequence is that it only eliminates ringing due to the application of the B-pulses, and does not reduce ringing from the A-pulse.

Several other methods for reducing the effects of ringing are known in the prior art. U.S. Pat. No. 6,498,484 to Sun et al., discusses a method in which two CPMG pulse sequences are used with variation of the static magnetic field. In the second pulse sequence, the static field amplitude is adjusted by an amplitude and time span selected to cause a 180 deg phase shift in the spin echo signals. Base line noise and ringing substantially cancels when the first and second signals are subtracted. In U.S. Pat. No. 6,121,774 to Sun et al., during a first time period of a single pulse sequence cycle, a first plurality of oscillating pulses is applied to a volume of formation. The subsequent measured signal comprises a ringing component and a plurality of spin-echoes. During a second time period of the single pulse sequence cycle, a second plurality of oscillating pulses are applied to the volume of formation and signals generated in the formation are measured. The measured signals comprise the ringing component and substantially exclude the spin-echoes. During the second time period, the spin-echoes and stimulated echoes may be eliminated by repeatedly applying a short pulse followed by a time delay in order to spoil the stimulated and echoes and spin-echoes. The signals measured during the first time period are corrected to eliminate the ringing component.

U.S. Pat. No. 6,377,042 to Menger et al., discusses a method of obtaining enhanced-resolution NMR data by merging, in the time domain, different NMR pulse echo trains into a single echo train. The input echo trains can be acquired with different inter-echo spacing, wait time, and signal-to-noise ratio parameters that are optimized to correspond to both fast and slow portions of the $T_2$ spectrum. The merged echo trains are inverted into complete $T_2$ spectra in a single step, the merged echo train typically carrying information about both relatively fast and relatively slow NMR signals.

In U.S. Pat. No. 6,541,969 to Sigal et al. an estimate of the ringing component of the signal can be obtained by combining two or more acquisition sequences in such a manner as to obtain an estimate of the ringing component of the signal. Alternatively, the ringing component of the signal is estimated by direct measurement using a separate NMR pulse sequence, which is a specific implementation is a standard CPMG pulse echo sequence without the leading 90° pulse. Such sequence will generally contain ringing but not any decay signals. Various signal processing or statistical methods are applied to remove the estimated ringing component from the acquisition sequences.

U.S. Pat. No. 6,570,381 to Speier et al. discusses using a series of cycles of measurement pulse sequences applied to a formation surround a borehole. Each pulse sequence includes an RF excitation pulse at several RF refocusing pulses. Spin echoes are received that contain spurious ringing signals from the excitation and refocusing pulses. For example, manipulating the polarities of the excitation and refocusing pulses can obtain the substantial cancellation of the spurious ringing from the excitation and refocusing pulses. Spin echo signals from corresponding spin echoes of each cycle are combined and substantially cancel the spurious ringing from the excitation and refocusing pulses of the pulse sequences. U.S. Pat. No. 6,518,757 to Speier discusses rotating the nuclear spins in a pulse sequence. A sequence of refocusing pulses is applied a period of time after termination of the excitation pulse to generate a plurality of echoes. The phase of the refocusing pulses is changed so that pairs of echoes in the echo train have opposite ringing phase. Echoes in the echo train having opposite ringing phase are added to cancel ringing in the echo train. The echo train can then be analyzed for amplitude and/or decay characteristics.

U.S. Pat. No. 6,466,013 to Hawkes et al. discusses a method of both maximizing a signal and minimizing RF power consumption. The timing and duration of the RF pulses are altered from conventional CPMG pulses. In an exemplary embodiment, a refocusing pulse having a spin tip angle less than 180° is applied with carrier phase shifted by typically $\pi/2$ radians with respect to the 90° tipping pulse. As a consequence, more of the nuclei originally tipped by 90° are refocused, resulting in larger echoes and reduced power consumption of the tool. An additional forced recovery pulse at the end of an echo train may be used to speed up the acquisition and/or provide a signal for canceling the ringing artefact.

U.S. Pat. No. 6,646,438 to Kruspe et al. discusses a method of acquiring NMR spin echo signal using pulse sequences having more than one interecho spacing By proper selection of the variable TE sequences, a desired resolution may be obtained for all expected components (short, medium, and long) while reducing the required time and the required power.

U.S. Pat. No. 6,204,663 to Prammer discusses a method for suppressing magneto-acoustic artifacts in NMR data using a cycle of pulse sequences characterized by a change in the measurement frequency between pulse sequences. In a preferred embodiment, the frequency change is chosen so that spurious signals induced by the excitation pulse may be significantly reduced by combining NMR signals from corresponding echoes received in response to each measurement frequency.

In the prior art, the PAPS sequence is useful only for reducing the ringing effect from the B-pulse. It would be desirable to have a method of removing ringing from both the A pulse and the B pulse in a situation where the ringing may be changing rapidly during the logging process. The present invention fulfills that need.

SUMMARY OF THE INVENTION

The present invention is a method for correcting for the effects of ringing produced by excitation and refocusing pulses in NMR data acquisition in earth formations. A Nuclear Magnetic Resonance tool conveyed in a borehole in the earth formation is used for pulsing the earth formation with a first pulse sequence having a first length, and with a plurality of additional pulse sequences having a length less than the first length. An estimate of the ringing is obtained from spin echo signals resulting from the additional pulse sequences. This estimate is then used to correct spin echo signals resulting from the first pulse sequence. The corrected spin echo signals may then be processed to obtain a parameter of interest of the earth formation. In one embodiment of the invention, the additional pulse sequences comprise clay bound water (CBW) sequences that may have durations less than 40 ms. The first and additional pulse sequences may include CPMG sequences or modified CPMG sequences having a tip angle of a refocusing pulse that is less than 180°. The additional pulse sequences may include pulse sequences having a plurality of pairs of phase alternated pairs (PAP) of pulse sequences and wherein the respective pairs of PAP sequences have a specified phase relationship to each other. This may be accomplished by frequency dithering. By forming a suitable vector sum of the signals, ringing from either the excitation pulse or the refocusing pulse may be estimated and cancelled.

The present invention is an apparatus for correcting for the effects of ringing produced by excitation and refocusing pulses in NMR data acquisition in earth formations. A magnet on a Nuclear Magnetic Resonance tool conveyed in a borehole in the earth formation polarized nuclear spins within a region of interest. An antenna on the NMR tool is used for pulsing the earth formation with a first pulse sequence having a first length and with a plurality of additional pulse sequences having a length less than the first length. A processor obtains an estimate of the ringing is obtained from spin echo signals resulting from the additional pulse sequences. The processor then uses this estimate to correct spin echo signals resulting from the first pulse sequence. The processor may then determine from the corrected spin echo signals a parameter of interest of the earth formation. In one embodiment of the invention, the additional pulse sequences may be clay bound water (CBW) sequences that may have durations less than 40 ms. The first and additional pulse sequences may include CPMG sequences or modified CPMG sequences having a tip angle of a refocusing pulse that is less than 180°. The additional pulse sequences may include pulse sequences having a plurality of pairs of phase alternated pairs (PAP) of pulse sequences and wherein the respective pairs of PAP sequences have a specified phase relationship to each other. This may be accomplished by frequency dithering. By forming a suitable vector sum of the signals, ringing from either the excitation pulse or the refocusing pulse may be estimated and cancelled.

BRIEF DESCRIPTION OF THE DRAWINGS

The present invention is best understood with reference to the accompanying figures in which like numerals refer to like elements and in which.

DETAILED DESCRIPTION OF THE INVENTION

Figure 1:
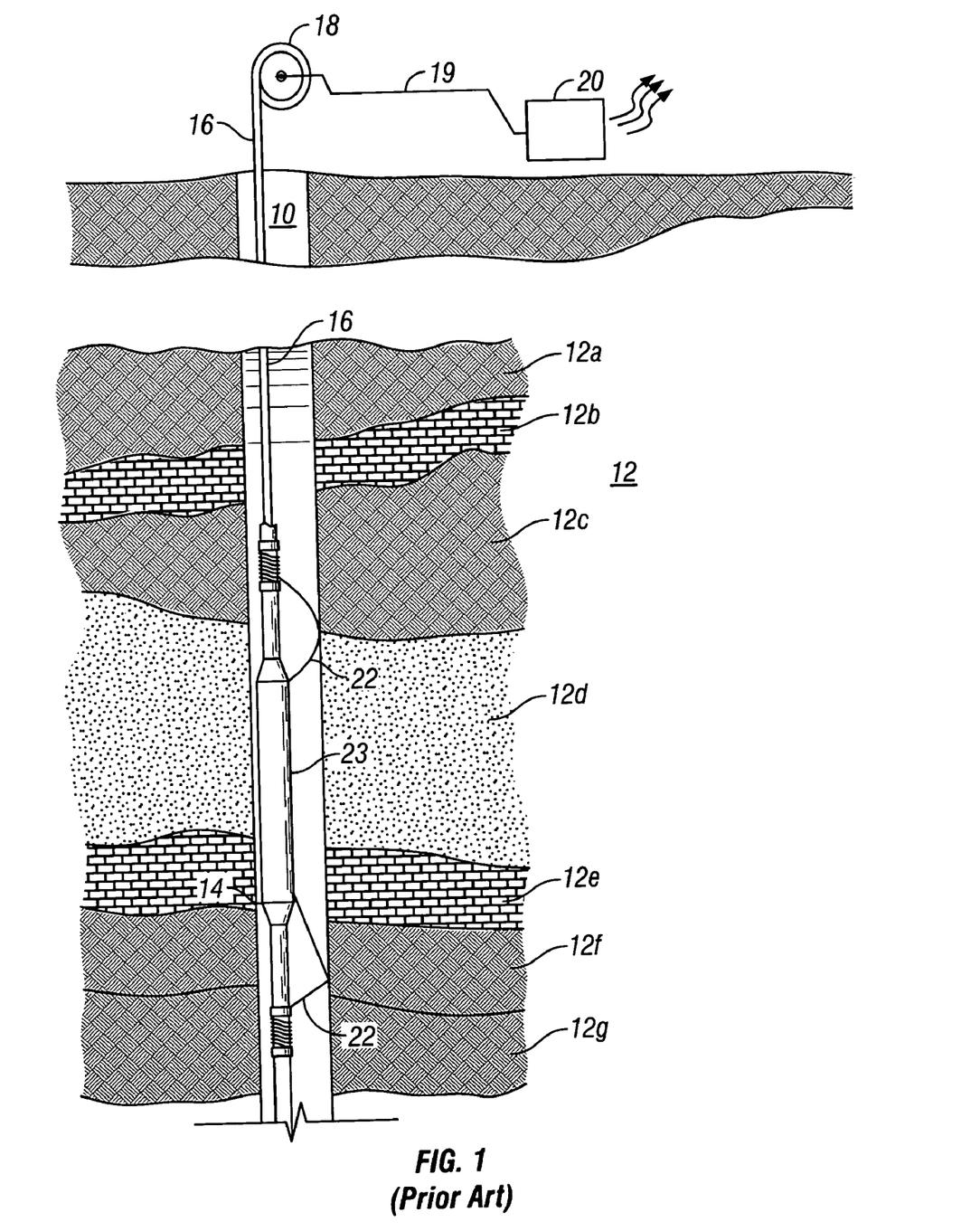
FIG. 1 (prior art) depicts diagrammatically an NMR logging tool in a borehole.

FIG. 1 depicts a borehole 10 drilled in a typical fashion into a subsurface geological formation 12 to be investigated for potential hydrocarbon producing reservoirs. An NMR logging tool 14 has been lowered into the hole 10 by means of a cable 16 and appropriate surface equipment (represented diagrammatically by a reel 18) and is being raised through the formation 12 comprising a plurality of layers 12a through 12g of differing composition, to log one or more of the formation's characteristics. The NMR logging tool may be provided with bowsprings 22 to maintain the tool in an eccentric position within the borehole with one side of the tool in proximity to the borehole wall. The permanent magnets 23 provide the static magnetic field . Signals generated by the tool 14 are passed to the surface through the cable 16 and from the cable 16 through another line 19 to appropriate surface equipment 20 for processing, recording, display and/or for transmission to another site for processing, recording and/or display. Alternatively, the processor may be located at a suitable position (not shown) downhole, e.g., in the logging tool 14.

Figure 2:
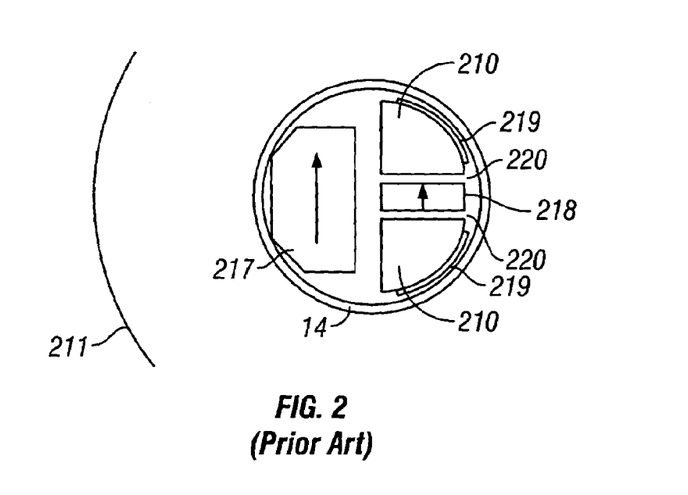
FIG. 2 (prior art) shows an exemplary configuration of magnets, antenna and shield suitable for use with the present invention.

FIG. 2 (prior art) schematically illustrates an exemplary embodiment of an apparatus suitable for use with the method of the present invention. This is discussed in detail in U.S. Pat. No. 6,348,792 to Beard et al. having the same assignee as the present invention; the contents of which are fully incorporated herein by reference. The tool cross-sectional view in FIG. 2 illustrates a main magnet 217, a second magnet 218 and a transceiver antenna comprising wires 219 and core material 210. The arrows 221 and 223 depict the polarization (e.g., from the South pole to the North pole) of the main magnet 217 and the secondary magnet 218. A noteworthy feature of the arrangement shown in FIG. 2 is that the polarization of the magnets providing the static field is towards the side of the tool, rather than towards the front of the tool (the right side of FIG. 2).

The second magnet 218 is positioned to augment the shape of the static magnetic field by adding a second magnetic dipole in close proximity to the RF dipole defined by the wires 219 and the soft magnetic core 210. This positioning moves the center of the effective static dipole closer to the RF dipole, thereby increasing the azimuthal extent of the region of examination. The second magnet 218 also reduces the shunting effect of the high permeability magnetic core 210 on the main magnet 217. In the absence of the second magnet, the DC field would be effectively shorted by the core 210. Thus, the second magnet, besides acting as a shaping magnet for shaping the static field to the front of the tool (the side of the main magnet) also acts as a bucking magnet with respect to the static field in the core 210. Those versed in the art will recognize that the bucking function and a limited shaping could be accomplished simply by having a gap in the core; however, since some kind of field shaping is required on the front side of the tool, in a preferred embodiment of the invention, the second magnet serves both for field shaping and for bucking. If the static field in the core 210 is close to zero, then the magnetostrictive ringing from the core is substantially eliminated.

Within the region of investigation, the static field gradient is substantially uniform and the static field strength lies within predetermined limits to give a substantially uniform Larmor frequency. Those versed in the art will recognize that the combination of field shaping and bucking could be accomplished by other magnet configurations than those shown in FIG. 2.

Still referring to FIG. 2, the transceiver wires 219 and core pieces 210 may be separated as far as possible towards the sides of the tool. This separation increases the transceiver antenna efficiency by increasing the effective RF dipole of the antenna and augments the shape of the RF magnetic field isolines so that they better conform to the static magnetic field isolines. The secondary magnet may be made of nonconducting material to minimize eddy currents induced by the RF field, thereby increasing the RF antenna efficiency. The antenna core may be made of a powdered soft magnetic material, other than ferrite, as disclosed in U.S. Pat. No. 6,452,388 to Reiderman et al. having the same assignee as the present invention and the contents of which are fully incorporated herein by reference. The antenna core has a high saturation flux density and comprises particles of powdered material small enough to be transparent to the RF magnetic field.

Figure 3:
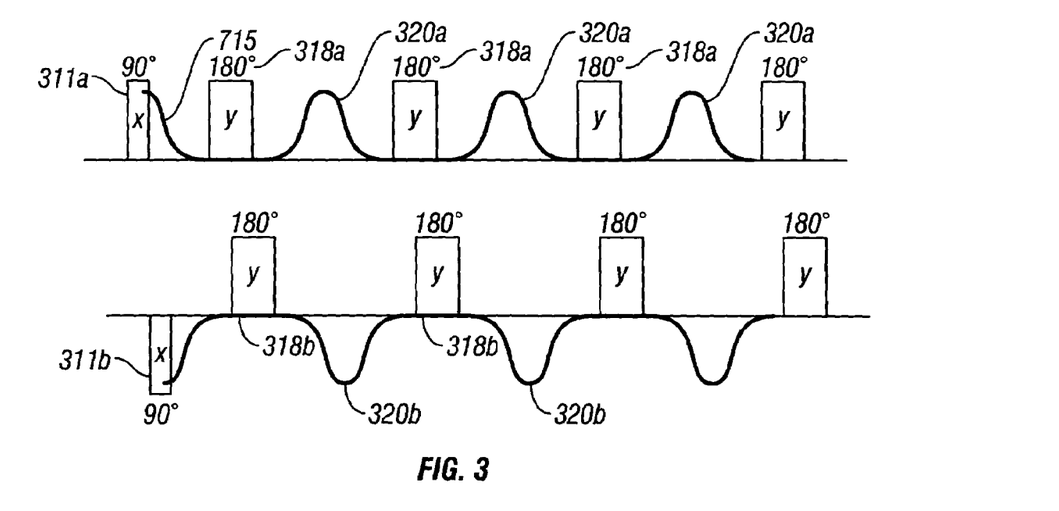
FIG. 3 (Prior Art) shows a PAPS sequence used in prior art.

The present invention typically comprises a long pulse acquisition sequence followed by a plurality of short pulse acquisition sequences. In typical PAPS acquisition (FIG. 3), two CPMG sequences are performed. A standard CPMG pulse sequence comprises the following:

$$W\text{-}A\text{-}t_s\text{-}B\text{-}(t_{cp}\text{-}echo\text{-}t_{cp}\text{-}B)_j \quad (7)$$

where W indicates a wait time prior to application of the A pulse, during which individual spins line up along the Z-axis defined by the static magnetic field, and A denotes an applied pulse that tilts the magnetic moment vector of the nuclear spins 90° into the x-y plane, typically through a rotation about the x-axis. The B pulses are refocusing pulses that rotate the nuclear spins 180° degrees, typically through a rotation about the y-axis. The first B pulse is applied a time $t_s$ after the A pulse, during which the spins dephase in the x-y plane. The subscript j denotes the index of the echoes and of the subsequent refocusing pulses in the sequence. Spin-echo signal (echo) typically occurs half-way between applied B-pulses, and are separated from each by a time-interval $t_{cp}$. At the start of any sequence, after waiting for a period W, the spin system is at substantially zero transverse magnetization and a positive longitudinal magnetization ($M_Z$) which is equal to or less than the full equilibrium magnetization. The rate at which nuclear spins align along the local static field axis (Z) during W is governed by the spin lattice relaxation time ($T_1$). By adjusting the wait period W information relating to $T_1$ can be obtained, as discussed in, among others, U.S. Pat. No. 5,023,551 to Kleinberg.

The first CPMG sequence of the PAP sequence has an A pulse (311a) for rotating the pulse into the x-y plane, followed by a sequence of B-pulses (318a). Echoes 320a are produces along the X-axis. The second CPMG sequence of the PAP sequence has, for instance, an A-pulse (311b) with opposite phase to pulse 311a along the x-axis. B-pulses (318b) are applied with same phase as in the first 318a. Echo 320b is opposite in polarity as echoes 320a. This second CPMG sequence is applied at a characteristic repetition time $tr_l$ after the first CPMG sequence is completed. Typically, $tr_l > T_1$, so that nuclear spins can substantially reorient themselves along the magnetization axis after completion of the first CPMG sequence. $T_1$ is typically on the order of several seconds in duration, so $tr_l$ is at least as long. Due to the duration of $tr_l$, many changes can occur in the local environment between PAP sequences that affect the noise. Just as importantly, the signal is also affected due to the duration of $tr_l$ due to motion of the measurement device over this time period. For instance, external particles that produce noisy signals can move into or out of the depth of investigation of the measuring devices. Also, the measuring device can be moved to a different position within the borehole during this time.

In situations where the ringing is varying on a time scale comparable to the time between the two halves of a phase-alternated-pair (PAP) acquisition, the PAP technique is unable to remove the ringing. In clay-bound-water (CBW) acquisitions PAP sequences are very close in time (~40 ms). Therefore, the ringing is easily removed. Use of the CBW acquisitions thereby enables measuring the ringing and correcting other CPMGs acquired at the same frequency and close in time to the CBW acquisition. These measurements can be used, for instance, to improve the signal-to-noise of the long echo train. Current CBW acquisitions use a frequency dithering technique to remove A-pulse ringing in which the dithering varies the phase of the ringing. When the data at the various frequencies are added, the ringing vector sums to zero. Using this technique also causes the B-pulse ringing to rotate (by about half as much the amount of A) so when the data are added, the measure of the B-pulse ringing is distorted.

The present invention uses a phase shifting technique based on frequency perturbation that is conceptually similar to the PAP technique of prior art in that it seeks to vary the relative phase of the non-formation signal, and hence to reduce the A-pulse ringing while simultaneously improving the signal-to-noise ratio. Frequency dithering techniques have been used, for example, in Prammer, and in U.S. patent application Ser. No. 10/675187 of Beard having the same assignee as the present invention and the contents of which are fully incorporated herein by reference. This is done by making small changes in the fundamental frequency of the NMR acquisition. In NMR the frequency and phase of the echo, and the frequency and phase of the demodulation in the detection system, are locked to the fundamental frequency of the pulse. Therefore, small changes in frequency cause little or no change in the phase of the detected echo. Also, in gradient field systems, small changes in frequency cause only small changes in the signal amplitude. Therefore, for small changes in frequency, i.e. those much less than the bandwidth of the RF carrier, the echo signal is effectively constant. However, the frequency of the non-formation signal is not locked to that of the acquisition sequence. So, by varying the frequency of the acquisition sequence, the phase of the non-formation signal will change, by a determinable amount given by:

$$\delta\phi = 2\pi \cdot \delta f \cdot t \quad (8)$$

where $\delta\phi$ is the change of phase, $\delta f$ is the change in frequency, and t is the time over which the phase difference evolves, i.e. the time between the effective center of the pulse, and the effective center of the detection window.

Upon maintaining a constant timing, the magnitude of the signal is expected to be essentially independent of the acquisition frequency. By perturbing the frequency a small amount, one varies the phase of the non-formation signal while keeping the amplitude of the non-formation signal and the phase and amplitude of the echo constant. It is therefore possible to eliminate the non-formation signal by performing acquisitions at two or more frequencies using frequency separations that will cause the non-formation signal to sum to zero.

It can be shown that if the vectors representing the phase of the non-formation signal are evenly distributed around the unit circle, they will sum to zero. If nf is the number of frequencies used, and the frequencies are separated by steps of size $\delta f$, the condition for the non-formation signal to sum to zero is as follows:

$$nf \cdot \delta f = \frac{m}{t} \quad (9)$$

where m is any integer that is not a multiple of nf. This is discussed in Beard.

Using general Eqn. (9), it is possible to consider specific cases. The simplest and most practical case is where two frequencies are applied (nf =2, m=1, t=TE). This case requires the least number of acquisitions. Setting m=1 minimizes $\delta f$, thereby setting up a situation which best suits the condition of small frequency changes. By noting that TE, the approximate time between an A-pulse and the first echo, is described as $2\tau$, one obtains the equation:

$$\delta f = \frac{1}{4 \cdot \tau} \quad (10)$$

Eqn. (10) is identical to the equation derived from the technique described in equation (1) of Prammer '663.

In a second and more general case, one can apply two frequencies, choosing the integer m to be an odd integer (nf=2, m=2n+1, t=TE=2$\tau$, where n is an integer). This definition of m ensures that it is not a multiple of 2, thereby leading to a necessary condition for the cancellation as described above. In this second case:

$$\delta f = \left(n + \frac{1}{2}\right) \cdot \frac{1}{2 \cdot \tau} \quad (11)$$

Eqn. (11) is identical to the equation derived from the technique described in equation (1A) of Prammer '663.

In a third case, which is the case of the present invention, three or more frequencies are used (nf >2, m=2, t=TE and TE/2). These parameter assignments in Eqn. (9) lead to the equation:

$$nf \cdot \delta f = \frac{2}{TE} = \frac{1}{TE/2} \quad (12)$$

Eqn. (12) above shows that if m is 2, and nf >2 (a necessary condition to avoid having m being a multiple of nf) the zero condition is met for evolution times of TE and TE/2. In other words the frequency dithering can be used to eliminate both A-pulse and B-pulse ringing. Using three pulse sequences having three separate frequencies (nf=3) enables the elimination of non-formation signals in a reduced time. Use of the preferred method in a multi-frequency measurement device enables further reduction of operation times over that of a shingle frequency measurement device. Similar reduction conditions can be achieved for any even value of m, but m=2 is a preferred value, based on its practicality. All other (larger) values of m are likely to require variations in frequency that are too large.

Further operation can be made in a fourth case, with three or more frequencies, with the condition of m=1 (nf >2, m=1, t=TE). Such an operating condition leads to the equation:

$$nf \cdot \delta f = \frac{1}{TE} \quad (13)$$

It is preferable to operate at three or more frequencies (nf >2), especially if time is available to apply more than 2 dithering frequencies (e.g. in a CBW package that has several CPMG sequences).

Figure 4:
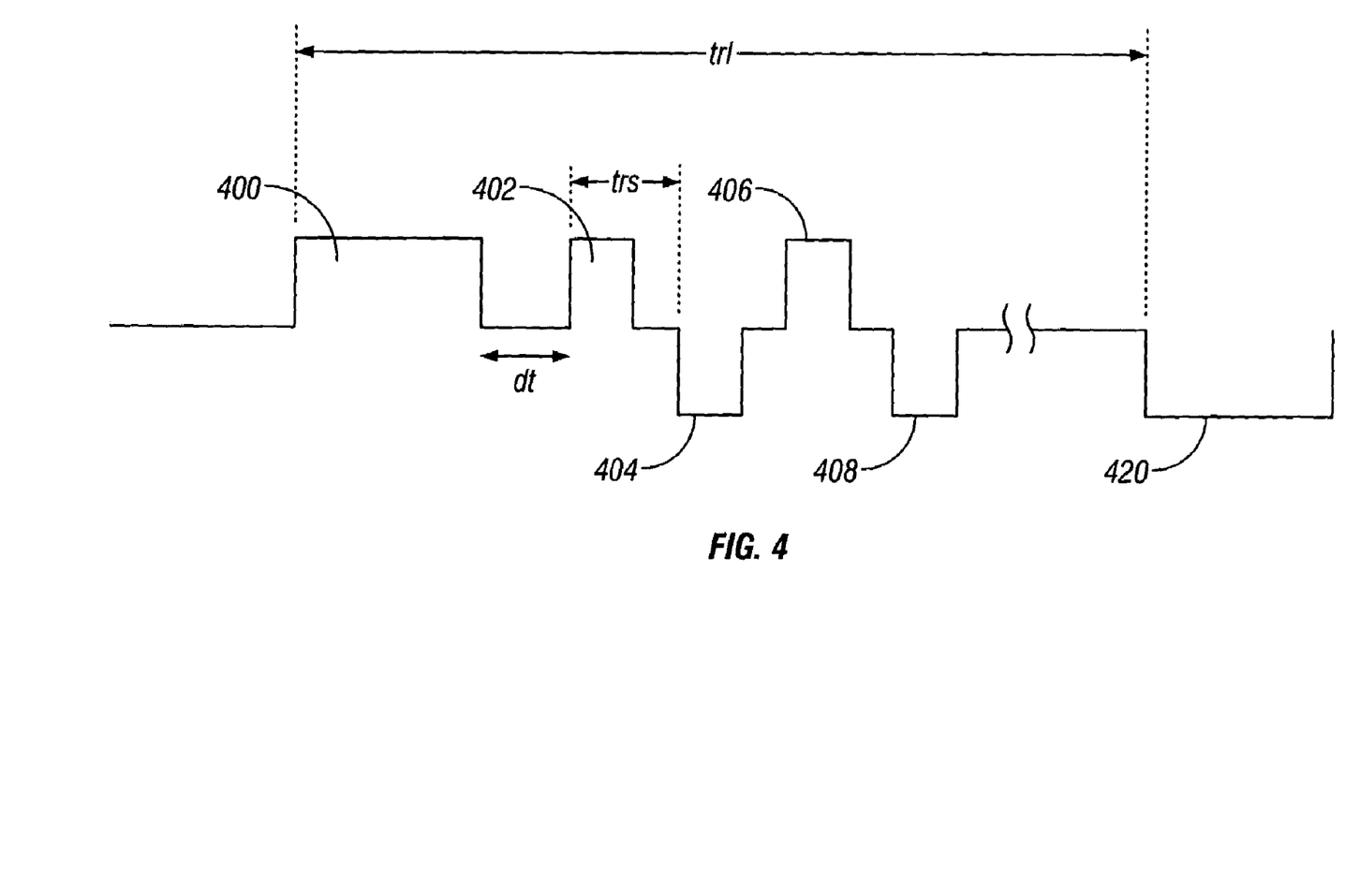
FIG. 4 shows a pulse sequence that is illustrative of the method of the present invention.

FIG. 4 shows an exemplary sequence of pulse sequences of the present invention. A pulse sequence 400 with a long recovery time tr1 is applied to obtain a sequence of echoes. The present invention enables obtaining measurement of the ringing signals from the A- and B-pulses much sooner after a long CPMG pulse 400 is applied, thereby leading to an improved reduction of the noise over prior art. In an exemplary embodiment of the present invention, shown in FIG. 4, long pulse sequence 400 is followed by pulse sequences with short recovery times. These pulse sequences with short recovery time are each comprised of two or more pairs of sequences each separated by short recovery time $tr_s$. It is quite common in NMR well-logging to follow a standard long recovery NMR sequence with a short recovery measurement that consists of two or more short sequences with a short recovery time. These short recovery measurements can be used, for example, to improve the signal-to-noise of the early echo train. Typically, these multiple sequences include PAPS within them. The repetition time for these sequences, $tr_s$, is much shorter than that of the standard measurements. Typically $tr_s$ is measured in tens of milliseconds, as opposed to the multiple seconds of $tr_l$. Experience has shown that these measurements are not corrupted even when the ringing is varying rapidly due to objects external to the instrument.

In FIG. 4 a long pulse sequence 400 is followed by a short delay time, dt. At the end of dt, a pulse sequence 402 with a short recovery time is applied. The pulse sequences with short recovery times are repeated with recovery time $tr_s$ between them, such that $tr_s < tr_l$. Consequently, while the pulse sequence 400 may correspond to fully recovered magnetization of nuclear spins in the static magnetic field, the pulse sequences with short recovery times are shown in FIG. 4 in part as 402, 404, 406, and 408. The number of short pulse sequences is typically much greater than that which is shown in FIG. 2, so FIG. 2 is not meant as a limitation on the invention. A typical short recovery pulse sequence gives rise to a plurality of echoes. Pulse sequence 402 is distinct from pulse sequence 404 by having a separate phase relation between A and B pulses. Typically, 402 and 404 form a PAP sequence. A variation in frequency can be applied to distinguish pulse 406 from pulse 402 and to distinguish pulse 408 from pulse 404. Also shown in FIG. 4 is an optional pulse sequence 420 with a long recovery time. 420 could be a phase alternated version of 400. Pulse sequences 400 and 420 may be viewed as a conventional PAP sequence. Use of this feature of the invention is discussed below.

The present invention takes advantage of another feature of the PAPS technique, in that the PAPS can be used not only to eliminate the ringing, but also to measure it. The present invention comprises the use of multiple, n pairs of PAPS sequences with recovery time performed a short time, dt, after a standard pulse sequence. An illustration of the present invention can be seen by considering two sets of short recovery measurements made shortly after a first standard measurement described above (FIG. 2). These measurements are made at the same applied frequency (f), with the same inter-echo time (TE), as the long measurement. Measured signals for the two short recovery measurements are written as $$\begin{bmatrix} m(t+dt+2i*tr_s) = e(t+dt+2i*tr_s) + r(t+dt+2i*tr_s) \\ m(t+dt+(2i+1)*tr_s) = e(t+dt+(2i+1)*tr_s) + \\ \qquad\qquad r(t+dt+(2i+1)*tr_s) \end{bmatrix}_{i=1,\ldots,n} \quad (14)$$

where m is the measured signal, e is the echo signal, r is the ringing signal, and i is an index over each of the n short sequences. Due to the comparatively short duration of $tr_s$, the instrument moves a fraction of an inch between each half of the PAP. Therefore the degree of change in the external environmental conditions is relatively small. The echo data can subsequently be extracted without corruption. By adding the PAPS instead of subtracting, again noting that the echo signal will change very little in the time $tr_s$, one can estimate the ringing as follows:

$$re(t+dt+(2i+0.5)*tr_s) = \frac{[ms(t+dt+2i*tr_s) + ms(t+dt+(2i+1)*tr_s)]}{2} \quad (15)$$

$$= \frac{[r(t+dt+2i*tr_s) + r(t+dt+(2i+1)*tr_s)]}{2}$$

$$= r\left(t+dt+n\frac{tr_s}{2}\right)$$

where re is the obtained estimated ringing, and n is the index of the sequence.

Time duration $$dt + n\frac{tr_s}{2}$$

is typically also short compared to the rate of change of ringing with time. This may not always be true, because this number can be as large as 1 second. However it is always true that $$dt + n\frac{tr_s}{2} \ll tr_i.$$

Therefore this ringing estimate $$re\left(t+dt+n\frac{tr_s}{2}\right)$$

is always a better estimator of the ringing at time, t, than the ringing in the following PAP which is at time $t+tr_l$. Since this estimate is created from multiple sequences, the noise level in the short recovery ringing estimate is typically much lower than that in the long recovery measurement. Thus, one can remove ringing from the long measurement by subtracting the estimate without significantly compromising the signal-to-noise level. Since it is a reasonable assumption that the ringing in each echo is the same, it is also possible to average the ringing estimate across all the echoes, and further improve the signal-to-noise ratio.

Figure 5:
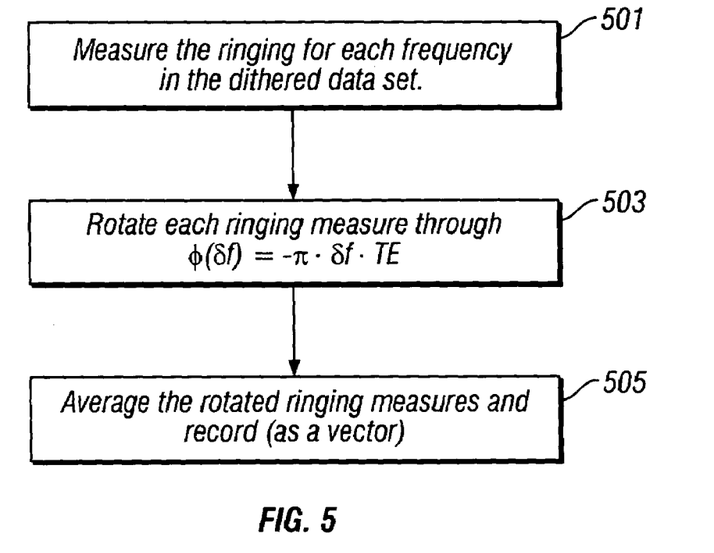
FIG. 5 shows a flowchart for reducing B-pulse ringing using short pulse sequences.

FIG. 5 shows a flowchart for obtaining the B-pulse ringing contribution. Due to the use of dithering methods, B-pulses ringing typically occurs at a several rotational phases. Removing the rotation in the ringing before performing an average enables a measurement of the B-pulse ringing. In Box 501, the ringing is measured in the normal way for each frequency in the perturbed data set, and maintained as a vector. In Box 503, each ringing measurement is rotated through an angle given by.

$$\phi(\delta f) = -\pi \cdot \delta f \cdot TE$$

where, $\delta f$ is the frequency at which the ringing is to be determined, and TE is the inter-echo time. Rotation can be achieved by multiplying the ringing vector by a rotation vector:

$$rot(\delta f) = e^{-i\pi \cdot \delta f \cdot TE}$$

where, i is the $\sqrt{-1}$. Table 1 shows an example (TE=0.6 ms) of the effect frequency has on the resultant rotation vector. In Box 505, the rotated ringing measures are averaged and recorded as a vector. Rather than averaging to obtain B-pulse ringing, one can alternatively subtract this ringing from each echo in any CPMG at the same frequency, same TE and close in time (<1 sec), before the standard PAP combination is performed.

TABLE 1

| Δf | Rotation Vector | |
|---|---|---|
| | Real | Imag |
| −2000 | −0.809 | −0.588 |
| −1900 | −0.905 | −0.426 |
| −1800 | −0.969 | −0.249 |
| −1700 | −0.998 | −0.063 |
| −1600 | −0.992 | 0.125 |
| −1500 | −0.951 | 0.309 |
| −1400 | −0.876 | 0.482 |
| −1300 | −0.771 | 0.637 |
| −1200 | −0.637 | 0.771 |
| −1100 | −0.482 | 0.876 |
| −1000 | −0.309 | 0.951 |
| −900 | −0.125 | 0.992 |
| −800 | 0.063 | 0.998 |
| −700 | 0.249 | 0.969 |
| −600 | 0.426 | 0.905 |
| −500 | 0.588 | 0.809 |
| −400 | 0.729 | 0.685 |
| −300 | 0.844 | 0.536 |
| −200 | 0.930 | 0.368 |
| −100 | 0.982 | 0.187 |
| 0 | 1.000 | 0.000 |
| 100 | 0.982 | −0.187 |
| 200 | 0.930 | −0.368 |
| 300 | 0.844 | −0.536 |
| 400 | 0.729 | −0.685 |
| 500 | 0.588 | −0.809 |
| 600 | 0.426 | −0.905 |
| 700 | 0.249 | −0.969 |
| 800 | 0.063 | −0.998 |
| 900 | −0.125 | −0.992 |
| 1000 | −0.309 | −0.951 |
| 1100 | −0.482 | −0.876 |
| 1200 | −0.637 | −0.771 |
| 1300 | −0.771 | −0.637 |
| 1400 | −0.876 | −0.482 |
| 1500 | −0.951 | −0.309 |
| 1600 | −0.992 | −0.125 |
| 1700 | −0.998 | 0.063 |
| 1800 | −0.969 | 0.249 |
| 1900 | −0.905 | 0.426 |
| 2000 | −0.809 | 0.588 |

Figure 6:
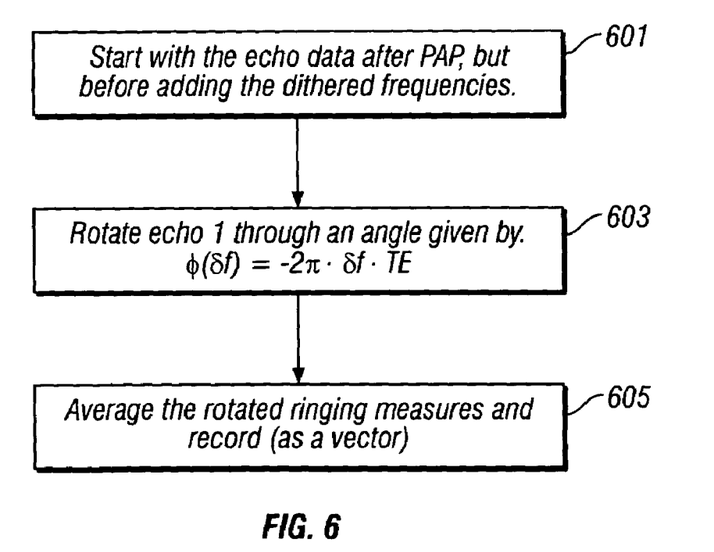
FIG. 6 shows a flowchart for reducing A-pulse ringing using short pulse sequences.

FIG. 6 shows a similar flowchart to that of FIG. 5 for obtaining A-pulse ringing. The ringing from A-pulse generally evolves for twice as long as the B-pulse ringing, and remains with the echo data after a PAP sequence. The most significant A-pulse ringing is associated with the first echo. It is also possible to measure the A-pulse ringing in echo 2 by doubling the rotation angle. In Box 601, one starts with the echo data after PAP, but before adding the dithered frequencies. In Box 803, the first echo (echo 1) is rotated through an angle given by.

$$\phi(\delta f) = -2\pi \cdot \delta f \cdot TE,$$

where δf is the actual frequency (the frequency at which the ringing is to be determined) and TE is the inter-echo time. This rotation is typically achieved by multiplying the ringing by the rotation vector $$rot(\delta f) = e^{-i \cdot 2\pi \cdot \delta f \cdot TE}$$

where, i is the $\sqrt{-1}$. In Box 605, the rotated ringing measures are averaged and recorded as a vector. This value can enable useful ringing log quality checks.

The advantage of the conventional PAP technique is that both halves of the PAP contain a signal. Therefore the process does not have an adverse effect on the signal-to-noise ratio. If we use ringing from CBW to remove ringing from, for instance, a $T_2$ echo train, the noise in the ringing measurement will be added to that of the echo train. This would not normally be an issue, because at least 32 echoes are used to calculate ringing in a CBW acquisition. Thus, the noise is reduced by a factor of 5.6 from that of the individual echoes, and it therefore has less than a 2% impact on the signal-to-noise ratio. However the noise may become an issue for the sum-of-echoes (SE) measurement. In the SE measurement the echoes are summed to get a significant reduction in the noise level, e.g. by a factor of 29 for 833 echoes. In such a case the ringing measurement will be the dominant source of noise. Even with 17 PAPs in a package, the noise from the ringing measurement is larger than that in the SE measurement.

Using the CBW to correct for ringing means that, if the noise level is acceptable, no vertical averaging is needed for the SE measurement. This gives the best possible vertical resolution for the measurement.

Referring back to FIG. 4, we show an exemplary embodiment in which calculations to determine ringing can be made using the measurements obtained from the application of the short pulse sequences. For instance, sequence 402 yields a measurement signal comprising echoes (E) plus ringing due to the A-pulse and ringing due to the B-pulse. The total obtained measurement signal is $M_1$=E+A+B. Sequence 404 yields an echo signal and a ringing signal from the A-pulse that is opposite to that of the ringing due to the B-pulse. Therefore, the total signal due to sequence 404 is $M_2$=−E−A+B. Sequence 406 comprises a different frequency than that of pulse 402. The total signal obtained from sequence 406 is $M_3$=E−A+B/90°, where the B-ringing pulse, being now along the X axis, has a phase shift of 90°. Sequence 408 comprises pulses at a different frequency than that of sequence 402. The total measured signal obtained from an application of pulse 408 is that of $M_4$=−E+A+B/90°, where, as with M3, the B-ringing pulse is offset by a phase shift of 90°.

Given the characteristic of the signals obtained from each pulse (402, 404, 406, and 408), a given combination of each pulse can be created to obtain a desired result. For instance, a combination of $M_1 - M_2 + M_3 - M_4$ yields four times the echo signal (4E). This combination eliminates both A-pulse ringing and B-pulse ringing.

Alternatively, it can be noted that a summation of M1 and M2 leads to the B-pulse ringing alone. Furthermore, the summation of M3 and M4 leads to the B-pulse ringing at a phase shift of 90°. A rotation of M3+M4 can be made and effectively combined with M1+M2.

It can also be noted that subtracting M3 from M1 leads to 2E+2A, whiles subtracting M4 from M2 leads to 2E−2A. A difference of these two equations can result in obtaining 4A, or a multiple of the A-pulse ringing alone.

Figure 7:
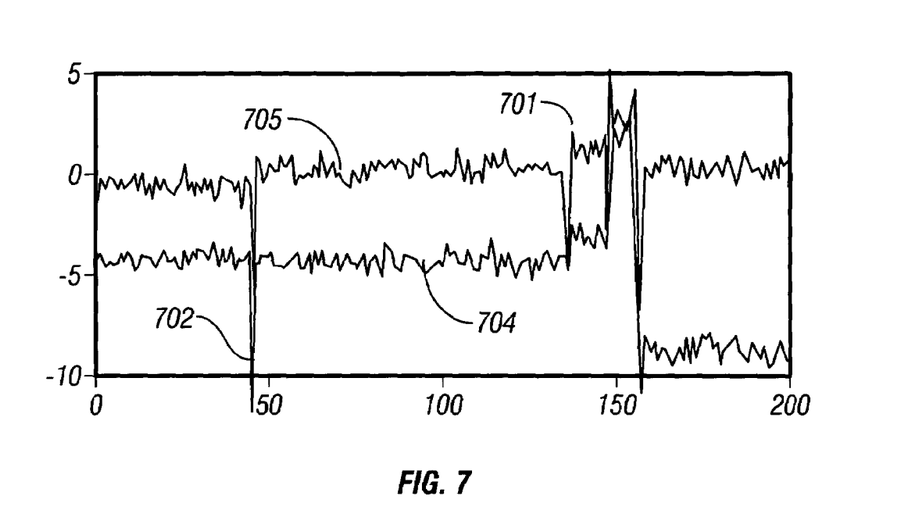
FIG. 7 shows field results for the method of the present invention at a frequency of 620 kHz.
Figure 8:
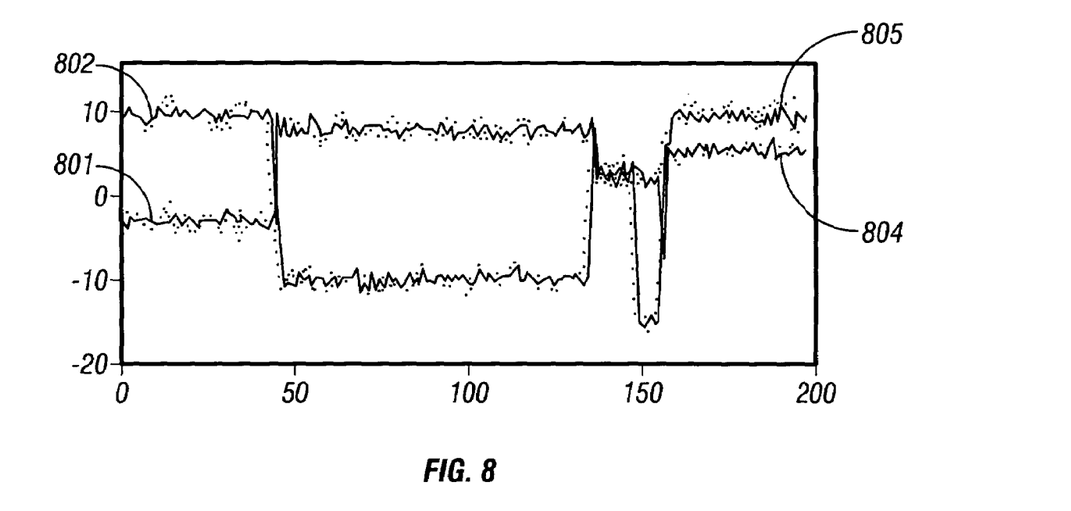
FIG. 8 shows field results for the method of the present invention at a frequency of 497 kHz.

FIGS. 7 and 8 show results of a field test of the method of the present invention. The method was tested on data collected in an Odessa test well. The tool was held stationary in three positions, enabling a calculation of ringing from the CBW and the regular $T_2$ echo train and also enabling observation of the statistics in the ringing measurement. The test was performed at two frequencies. FIG. 7 shows the results obtained at the first frequency (f=620 kHz, with 13 dithered frequencies). There are 833 echoes used for the ringing estimation from the $T_2$ train. Curve 701 shows the results obtained from channel 1 from CBW (short) sequences and curve 702 shows the results obtained from channel 2 from CBW sequences. Curve 704 shows the results obtained from channel 1 from T2 (long) sequences. Curve 705 shows the results obtained from channel 2 from T2 (long) sequences. Even though the noise in the ringing measurement is much lower than a typical per-echo-noise, it is large compared with a SE-type measurement.

FIG. 8 shows the results obtained at the first frequency (f=497 kHz, with 12 dithered frequencies). There are 50 echoes used for the $T_2$ train. Curve 801 shows the results obtained from channel 1 from CBW (short) sequences and curve 802 shows the results obtained from channel 2 from CBW sequences. Curve 804 shows the results obtained from channel 1 from T2 (long) sequences. Curve 805 shows the results obtained from channel 2 from T2 (long) sequences. The noise in the ringing measurement is lower than that in a SE-type measurement.

Once the effects of non-formation signals such as ringing from the A-pulse and the B-pulse have been estimated, they can be removed. The corrected signals can then be processed using prior art methods to obtain parameters of interest of the earth formation such as a $T_2$ distribution, total porosity, bound volume irreducible (BVI), clay bound water (CBW), bound volume movable (BVM), and a $T_1$ distribution.

It is to be noted that the pulse sequences that may be used with the present invention may include conventional CPMG sequences as well as modified CPMG sequences having a reduced refocusing B pulse angle. Such modified CPMG sequences have been disclosed in U.S. Pat. No. 6,163,153 to Reiderman et al., having the same assignee as the present invention and the contents of which are fully incorporated herein by reference; and in U.S. patent of Hawkes. It should further be noted that the invention has been discussed with reference to a wireline tool. This is not a limitation of the invention, and the method could also be used on a NMR logging tool conveyed on a drilling tubular such as drill-string or coiled tubing into the earth formation. The method can also be used on a NMR logging tool conveyed on a slickline.

Returning now to FIG. 4, we note that the combination of 400 and 420 defines a conventional PAP sequence with a long recovery time. An independent estimate of the ringing can be made from 400 and 420 using prior art methods. In a situation where the formation (and the nature of the ringing) is not changing, the estimate of ringing from the pair 400/420 may be superior to the estimate of ringing obtained from the short recovery sequences 402, 404, 406 . . . 408. However, in a situation where the ringing is changing as the logging tool is conveyed through the borehole, the short recovery methods will give a better estimate of the time varying ringing. Hence a comparison of the ringing estimate from the short and long recovery PAP sequence provides a useful indication of changes in the formation. It should be pointed out that in FIG. 4, the short recovery pulse sequences have been shown with a duration that is shorter than the long recovery pulse sequence 400. This is not to be construed as a limitation of the method of the present invention.

While the foregoing disclosure is directed to the specific embodiments of the invention, various modifications will be apparent to those skilled in the art. It is intended that all such variations within the scope and spirit of the appended claims be embraced by the foregoing disclosure.

What is claimed is:

1. A method for correcting signals received from an earth formation using a Nuclear Magnetic Resonance (NMR) tool in a borehole in said earth formation, the method comprising:

(a) exciting said earth formation with a first pulse sequence having a first recovery time;

(b) exciting said earth formation with a plurality of additional pulse sequences having a second recovery time less than said first recovery time;

(c) determining from spin echo signals resulting from said additional pulse sequences an estimate of a non-formation signal; and (d) correcting spin echo signals resulting from said first pulse sequence using said estimate.

2. The method of claim 1 wherein at least one of said additional pulse sequences has a duration less than a duration of said first pulse sequence.

3. The method of claim 1 wherein said second recovery time corresponds to partial recovery of nuclear spins in said earth formation.

4. The method of claim 1 wherein said additional pulse sequences comprise clay bound water (CBW) sequences.

5. The method of claim 1 wherein said additional pulse sequences have durations less than 40 ms.

6. The method of claim 1 wherein said first pulse sequence and said additional pulse sequences comprise CPMG sequences.

7. The method of claim 1 wherein said first pulse sequence and said additional pulse sequences comprise modified CPMG sequence having a tip angle of a refocusing pulse that is less than 180°.

8. The method of claim 1 wherein said additional pulse sequences comprise pulse sequences having a plurality of pairs of phase alternated pairs (PAP) of pulse sequences.

9. The method of claim 6 wherein said plurality of pairs of PAP sequences have a specified phase relationship to each other.

10. The method of claim 8 wherein the number of said pairs of PAP sequences nf, frequency shift between said pairs of PAP sequences δf are related according to:

$$nf \cdot \delta f = \frac{m}{t}$$

where m is any integer that is not a multiple of nf.

11. The method of claim 8 wherein said non-formation signal comprises a ringing from a refocusing pulse.

12. The method of claim 11 wherein estimating said ringing from said refocusing pulse further comprises:

(i) separately estimating a ringing from each one of said plurality of phase alternated pairs;

(ii) forming a vector sum of said separate estimates.

13. The method of claim 8 wherein said non-formation signal comprises a ringing from an excitation pulse.

14. The method of claim 13 wherein estimating said ringing from said excitation pulse further comprises:

(i) separately estimating an echo signal from each one of said plurality of phase alternated palm; and (ii) forming a vector sum of said separate estimates of said echo signal.

15. The method of claim 1 further comprising processing said corrected spin echo signals for determining at least one of (i) a $T_2$ distribution, (ii) total porosity, (iii) bound volume irreducible, (iv) a $T_1$ distribution, (v) clay bound water, (vi) bound water moveable, and (vii) a sum of echos.

16. The method of claim 1 further comprising conveying said NMR tool into said earth formation on one of (i) a wireline, (ii) a drilling tubular, and, (iii) a slickline.

17. The method of claim 1 further comprising:

(i) exciting said earth formation with a second pulse sequence having a recovery time substantially equal to said first recovery time, said second pulse sequence forming a phase alternated pair with said first pulse sequence; and (ii) determining from spin echo signals resulting from said first and second pulse sequences an additional estimate of said non-formation signal.

18. The method of claim 17 further comprising:
(A) comparing said estimate and said additional estimate of said non-formation signal; and
(B) using a result of said comparison as an indication of a change in said earth formation between positions of said NMR tool at excitation with said first and second pulse sequences.

19. An apparatus for conducting logging operations in a borehole in an earth formation, the apparatus comprising:
(a) a magnet on a Nuclear Magnetic Resonance (NMR) tool which polarizes nuclear spins in a region of interest in the earth formation;
(b) an antenna on the NMR tool which:
(A) excites said earth formation with a first pulse sequence having a first recovery time;
(B) excites said earth formation with a plurality of additional pulse sequences having a recovery time less than said first recovery time;
(c) a processor which:
(C) determines from spin echo signals resulting from said additional pulse sequences an estimate of a non-formation signal, and corrects spin echo signals resulting from said first pulse sequence using said estimate.

20. The apparatus of claim 19 wherein said additional pulse sequences comprise clay bound water (CBW) sequences.

21. The apparatus of claim 19 wherein said additional pulse sequences have durations less than 40 ms.

22. The apparatus of claim 21 wherein said processor further determines from said corrected spin echo signals at least one of (i) a $T_2$ distribution, (ii) total porosity, (iii) bound volume irreducible, (iv) bound water movable, (ii) clay bound water, (vi) a $T_1$ distribution and (vii) a sum of echos.

23. The apparatus of claim 19 wherein said first pulse sequence and said additional pulse sequences comprise CPMG sequences.

24. The apparatus of claim 19 wherein said first pulse sequence and said additional pulse sequences comprise modified CPMG sequence having a tip angle of a refocusing pulse that is less than 180°.

25. The apparatus of claim 19 wherein said additional pulse sequences comprise pulse sequences having a plurality of pairs of phase alternated pairs (PAP) of pulse sequences.

26. The apparatus of claim 25 wherein said plurality of pairs of PAP sequences have a specified phase relationship to each other.

27. The apparatus of claim 26 wherein said processor estimates ringing caused by an excitation pulse by:
(i) separately estimating an echo signal from each one of said plurality of phase alternated pairs; and
(ii) forming a vector sum of said separate estimates of said echo signal.

28. The apparatus of claim 25 wherein the number of said pairs of PAP sequences nf, frequency shift between said pairs of PAP sequences δf are related according to:

$$nf \cdot \delta f = \frac{m}{t}$$

where m is any integer that is not a multiple of nf.

29. The apparatus of claim 25 wherein said non-formation signal comprises a ringing caused by a refocusing pulse.

30. The apparatus of claim 25 wherein said non-formation signal comprises a ringing caused by an excitation pulse.

31. The apparatus of claim 25 wherein said processor estimates ringing caused by an refocusing pulse by:
(i) separately estimating a ringing from each one of said plurality of phase alternated pairs;
(ii) forming a vector sun of said separate estimates.

32. The apparatus of claim 19 further comprising a conveyance device for conveying said NMR tool into said borehole, said conveyance device selected from (i) a wireline, (ii) a drilling tubular, and, (iii) a slickline.

33. The apparatus of claim 19 wherein said transmitter further excites said earth formation with a second pulse sequence having a recovery time substantially equal to said first recovery time, said second pulse sequence forming a phase alternated pair with said first pulse sequence; and wherein said processor further determines from spin echo signals resulting from said first and second pulse sequences an additional estimate of said non-formation signal.

34. The apparatus of claim 33 wherein said processor further:
(i) compares said estimate and said additional estimate of said non-formation signal; and
(ii) provides an indication of a change in said earth formation between positions of said NMR tool at excitation with said first and second pulse sequences.

* * * * *